United States Patent [19]

Diehl

[11] 4,049,824

[45] Sept. 20, 1977

[54] CETYL MYRISTOLEATE

[76] Inventor: Harry Weldon Diehl, 4424 Oak Hill Road, Rockville, Md. 20853

[21] Appl. No.: 682,540

[22] Filed: May 3, 1976

[51] Int. Cl.$^2$ .......................... A61K 31/23; C11C 3/02
[52] U.S. Cl. .............................. 424/312; 260/410.9 R
[58] Field of Search .................. 424/312; 260/410.9 R

[56] References Cited

U.S. PATENT DOCUMENTS 3,194,822  7/1965  Neiswerder ........................ 260/410.9
3,427,344  2/1969  Koshigoe et al. ................. 260/410.9

OTHER PUBLICATIONS

Chem. Abst. 70 - 69470r (1969).

Primary Examiner—Stanley J. Friedman
Attorney, Agent, or Firm—John C. Smith, Jr.

[57] ABSTRACT

A method is described for immunizing against inflammatory rheumatoid arthritis in mammals and for immunizing against and relieving at least one of the symptoms of inflammatory rheumatoid arthritis in mammals.

10 Claims, No Drawings

CETYL MYRISTOLEATE

The present invention relates to a method for immunizing against inflammatory rheumatoid arthritis in mammals and for immunizing against and relieving at least one of the symptoms of inflammatory rheumatoid arthritis in mammals by administering parenterally an immunologically or therapeutically effective amount of cetyl myristoleate

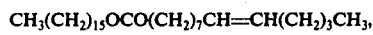

to a method of preparing the pharmacologically active cetyl myristoleate by extracting the compound from the tissues of mice and to the compound itself. Osteoarthritis is one of the oldest and most common inflammatory diseases in mammals. It occurs at all ages. Studies show that 97% of all persons over age 60 have an arthritic condition which can be observed by X-ray. The most common symptoms of arthritis are pain, fever and inflammation, and it is the No. 1 crippling disease in man.

An object of the present invention is to provide a method for immunizing against inflammatory rheumatoid arthritis in mammals and to immunize against and relieve the symptoms of inflammatory rheumatoid arthritis in mammals.

Another object of the invention is to inhibit the symptoms, such as pain, fever and inflammation associated with inflammatory rheumatoid arthritis in mammals by administering parenterally cetyl myristoleate extracted from the tissues of mice.

A still further object of the present invention is a method for preparing a compound useful in immunizing against inflammatory rheumatoid arthritis and in inhibiting the appearance of the symptoms thereof by extraction from the tissues of mice.

These and other objects will become apparent in the following detailed description of the invention.

It is well known that Freund's adjuvant will induce poly-arthritis in rats but not in mice. It has been common practice to test various compounds and compositions in laboratories to determine their effectiveness in relieving the symptoms of inflammatory rheumatoid arthritis by administering test compounds or compositions to rats having poly-arthritis induced previously by administering Freund's adjuvant. It was hypothesized that mice must contain some protective factor or mechanism which prevented the inducement of poly-arthritis in mice.

In accordance with the present invention a substance has been isolated from mice which, when administered to rats, essentially prevents the formation of poly-arthritis and the resultant symptoms when the rats are subsequently injected with Freund's adjuvant. The substance was isolated by extracting homogenized whole mice with methylene chloride. Upon purification of this extracted substance it was identified as cetyl myristoleate. The following example describes in greater detail the isolation of the effective substance from mice.

EXAMPLE I

Seventy-nine mice totalling 2300 grams were macerated in an electric blender in batches of about eight mice, each batch being macerated in 400 ml methylene chloride. The final blend was poured into a 4 liter beaker. The blend was stirred until the methylene chloride separated, then the mixture was filtered under light suction through a large Buchner funnel containing filter paper covered by a thin layer of Filter-Cel. The resultant precipitate was washed with two 100 ml portions of methylene chloride. The combined filtrate and washings were separated from a top layer of water after which the methylene chloride was filtered again. This filtrate was concentrated in vacuo to a thin syrup of 167 grams which was treated with four parts of acetone and then left at $-5°$ C for 3 days with brief stirring each day.

The mixture was filtered using Buchner filter paper with a layer of Filter-Cel and light suction. The precipitate was washed with four 25 ml portions of $-5°$ C acetone. The combined filtrate and washings were concentrated in vacuo to a thin syrup of 121 grams. This material was dissolved in 500 ml of 20:1 legroin ($20°-40°$ C), dry ether and chromatographed on 2500 ml 40–325 mesh ASTM silica gel in an appropriate column using the 20:1 legroin-ether mixture as eluent. One 1500 ml "blank" and then eleven 100 ml and six 200 ml fractions were collected.

Fraction Nos. 3–15 inclusive were combined and filtered in vacuo through 120 grams of Darco-X. The filtrate was concentrated in vacuo to a syrup of 0.15 gram. The Darco-X was further washed with several portions of methylene chloride. The 0.15 gram of syrup was dissolved in these washings which were concentrated in vacuo to a syrup of 0.8 gram of crude material. This was chromatographed using 350 ml of silica gel, 70–325 mesh ASTM using 40:1 carbon tetrachloride-ether as eluent.

Fraction Nos. 67–79 of 7 ml each gave 0.4 gram of material which was rechromatographed with 125 ml of silica gel using 60:1 carbon tetrachloride-ether in 2.5 ml fractions.

Fraction Nos. 117–127 gave 0.15 gram of purified syrup which proved to be principally the desired "immunity factor", cetyl myristoleate ($v_{max}^{neat}$ 1782 cm$^{-1}$). Extensive thin-layer chromatography and frequent bioassays were used throughout to monitor the isolation and purification of the compound.

The following example describes the steps taken to identify the cetyl myristoleate product of Example I.

EXAMPLE II

A mixture of 0.15 gram of the material obtained in Example I was heated with 2 ml of acetone and 3 ml of 10% sodium hydroxide solution under reflux with stirring for fourteen hours and then treated with 0.7 ml of 12 M HCl. Extractions were made with four 5 ml portions of methylene chloride followed by drying with Na$_2$SO$_4$ and then evaporated with methylene chloride in vacuo. The 0.14 gram of material recovered was chromatographed on 140 ml of silica gel with methylene chloride as eluent. A 400 ml and one hundred ten 6 ml fractions were collected.

Fraction Nos. 20–55 gave 40 mg of cetyl alcohol having a melting point of $49°-50°$ C after recrystallization from ethanol. The analysis calculated for C$_{16}$H$_{34}$O is

C — 79.3%
H — 14.1%

The analysis found was

C — 79.2%
H — 14.3%

Fraction Nos. 89–110 produced 60 mg of a syrup which was further purified by chromotography. The resultant acid gave ($v_{max}^{neat}$ 1712, 1722 (sh cm$^{-1}$). The analysis calculated for $C_{14}H_{26}O_2$ is C — 74.4%
H — 11.6%
Neut. equiv. — 226.3

What was found is as follows:

C — 74.1%
H — 169%
Neut. equiv. — 225.5

Both the cetyl myristoleate extracted from the tissues of mice as described in Example I and cetyl myristoleate prepared synthetically as described in Example III have been found to be effective in immunizing against rheumatoid arthritis and the symptoms thereof.

EXAMPLE III

A charge of 150 mg of cetyl alcohol, 150 mg of myristoleic acid, 50 mg of p-toluenesulfonic acid monohydrate of 20 ml of benzene were heated together under reflux conditions for four hours and then washed with a —0% sodium hydroxide solution. The benzene layer was recovered, dried and evaporated in vacuo.

This procedure produced 300 mg of a mobile oil which was identified as cetyl myristoleate ($v_{max}^{neat}$ 1782 cm$^{-1}$) (nuclear-magnetic-resonance and infrared spectroscopy).

EXAMPLE IV

Following the procedure set out in Example II, 150 mg of cetyl alcohol obtained in Example III and 150 mg of the acid obtained in Example II produced 300 mg of an ester ($v_{max}^{neat}$ 1782 cm$^{-1}$) which was identified by similar means with the products in Examples I and III.

EXAMPLE V

The cetyl myristoleate or "immunity factor" produced both synthetically and by isolation from whole mice, respectively, were administered parenterally in mineral oil as a compatible carrier to male rats (Sprague Dawley Strain) ranging in weight between 140 and 200 grams. It is not necessary, however, that a carrier be used since cetyl myristoleate is itself an oil.

One set of rats was innoculated subcutaneously with 1.0 ml each of a mixture of mineral oil and 0.05 gm of the immunity factor. Twenty-four hours later the rats were innoculated with Bacto m. Butyricum (Disco 0640-33). A control group received only the Butyricum.

Another set of rats were given 1.0 ml each of a mixture of mineral oil containing 0.075 gm of the synthetically produced cetyl myristoleate. Two days later the rats were innoculated with Bacto m. Butyricum (Disco 0640-33). Another control group received only the Butyricum.

The rats in both control groups developed severe poly-arthritis during the following 10 to 18 day period which persisted through 32 days. All of these rats gradually lost weight.

About 70% of the first group (those treated with "immunity factor" plus Butyricum) were completely protected from the poly-arthritis. They showed no swelling or other symptoms. The other 30% were partially protected during the 32-day period.

All of the second group (those treated with synthetically produced cetyl myristoleate plus Butyricum) were protected from the poly-arthritis and showed a steady gain in weight.

It was found that the purer the cetyl myristoleate the more dramatic were the results in protecting the rats from poly-arthritis. Also, an effective dosage of cetyl myristoleate or "immunity factor" preferably ranges between 0.05 and 0.75 gm for each 140–200 gms weight of the animal. However, doses smaller than and greater than this range will effectively immunize mammals against inflammatory rheumatoid arthritis and immunize against and relieve the symptoms thereof such as pain, fever and inflammation.

Thus havig described the invention in detail, it will be understood by those skilled in the art that certain modifications and variations may be made without departing from the spirit and scope of the invention as described herein and defined in the appended claims.

I claim:

1. A method of relieving and inhibiting the symptoms of inflammatory rheumatoid arthritis in mammals which comprises the parenteral administration to a mammal of an effective amount of cetyl myristoleate.

2. A method according to claim 1 wherein said cetyl myristoleate is extracted from the tissues of mice.

3. A method according to claim 1 wherein said cetyl myristoleate is administered with a compatible pharmaceutical carrier.

4. A method according to claim 3 wherein said compatible pharmaceutical carrier is mineral oil.

5. A method according to claim 1 wherein about 0.05–0.75 gm of cetyl myristoleate is administered for each 140–200 gms weight of the animal.

6. A method for preparing a concentrate containing cetyl myristoleate useful for relieving and inhibiting the symptoms of inflammatory rheumatoid arthritis in mammals comprising macerating the tissues of mice to form a macerated material, extracting said macerated material with a solvent to form an extract and concentrating said extract to form said concentrate containing cetyl myristoleate.

7. A method according to claim 6 wherein said macerated material is extracted with methylene chloride.

8. A method according to claim 6 comprising the further step of diluting said extract with a compatible pharmaceutical carrier.

9. A method according to claim 8 wherein said compatible pharmaceutical carrier is mineral oil.

10. The compound, cetyl myristoleate, having the structure

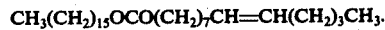

$$CH_3(CH_2)_{15}OCO(CH_2)_7CH=CH(CH_2)_3CH_3.$$

* * * * *

UNITED STATES PATENT OFFICE
CERTIFICATE OF CORRECTION

Patent No. 4,049,824           Dated September 20, 1977

Inventor(s) Harry Weldon Diehl

It is certified that error appears in the above-identified patent and that said Letters Patent are hereby corrected as shown below:

Column 3, line 8 should read:

-- H — 11.9% --

Column 3, line 21 should read:

-- 10% sodium hydroxide solution. The benzene layer --

Signed and Sealed this

Ninth Day of May 1978

[SEAL]

Attest:

RUTH C. MASON
Attesting Officer

LUTRELLE F. PARKER
Acting Commissioner of Patents and Trademarks